US00PP37704P2

(12) United States Plant Patent
Nakai et al.

(10) Patent No.: US PP37,704 P2
(45) Date of Patent: Sep. 22, 2026

(54) ***FRAGARIA L.* PLANT NAMED 'YUKAGUYA'**

(50) Latin Name: ***Fragaria* L.**
Varietal Denomination: YUKAGUYA

(71) Applicants: NATIONAL AGRICULTURE AND FOOD RESEARCH ORGANIZATION, Tsukuba (JP); OREC CO., LTD, Hirokawa-machi (JP)

(72) Inventors: Yusuke Nakai, Tsukuba (JP); Kazuyoshi Sone, Tsukuba (JP); Toshiro Fujita, Tsukuba (JP); Masahiro Misumi, Tsukuba (JP); Kota Hidaka, Tsukuba (JP); Minori Endo, Tsukuba (JP); Masafumi Seki, Hirokawa-machi (JP)

(73) Assignees: NATIONAL AGRICULTURE AND FOOD RESEARCH ORGANIZATION, Tsukuba (JP); OREC CO., LTD, Hirokawa-machi (JP)

( * ) Notice: Subject to any disclaimer, the term of this patent is extended or adjusted under 35 U.S.C. 154(b) by 0 days.

(21) Appl. No.: 19/362,560

(22) Filed: Oct. 20, 2025

(51) Int. Cl.
*A01H 5/08* (2018.01)

(52) U.S. Cl.
USPC ..... Plt./208

(58) Field of Classification Search
USPC ..... Plt./208
CPC ..... A01H 6/7409; A01H 5/08
See application file for complete search history.

*Primary Examiner* — Keith O. Robinson
(74) *Attorney, Agent, or Firm* — Seckel IP, PLLC

(57) ABSTRACT

This new strawberry plant 'YUKAGUYA' has plant growth habit in upright, high plant height, large leaf, long petiole, medium to many flowers per Inflorescence, medium to large flower diameter, large to very large fruit, conical fruit shape, vivid reddish orange fruit color, firm fruit, vivid reddish orange flesh, early fruit ripening, high to very high soluble solid contents, low to medium acidity, and highly resistant to *Colletotrichum fragariae.*

3 Drawing Sheets

Common name: Strawberry.
Botanical classification: *Fragaria* L.
Variety denomination: 'YUKAGUYA'.

BACKGROUND OF THE NEW VARIETY

The present invention relates to a new and distinct variety of Strawberry, *Fragaria* L., which has been given the variety denomination 'YUKAGUYA'.

ORIGIN OF THE VARIETY

The parent varieties are '12164-02' (female parent) (not patented), and 'KUMAMOTO VS03' (male parent) (PVP granted in Japan, No. 25,611), respectively.

The variety was developed and propagated in Kurume, Fukuoka, Japan.

The variety was reproduced asexually by vegetative reproduction, also in Kurume, Fukuoka, Japan.

In 2016, The parent varieties were crossed, the resulting seeds were sown, and the grown individuals were selected.

In 2022, The line selection and performance test were carried out.

In 2024, The selected line 16073-01 were confirmed to have high fruit hardness, relatively high yields, and early maturity. Furthermore, growing tests were conducted in a plant factory with artificial light, and the excellent fruit quality and yields confirmed its suitability for cultivation in plant factory.

In 2025, the variety was named 'YUKAGUYA' and PVP application No. 37,886 was filed on Feb. 19, 2025, in the Plant Variety Protection Office in Japan.

Growing the variety does not require special conditions or treatments.

The variety is currently mainly intended for fruit production.

SUMMARY OF THE VARIETY

This new strawberry plant 'YUKAGUYA' has plant growth habit in upright, high plant height, large leaf, long petiole, medium to many flowers per Inflorescence, medium to large flower diameter, large to very large fruit, conical fruit shape, vivid reddish orange fruit color, firm fruit, vivid reddish orange flesh, early fruit ripening, high to very high soluble solid contents, low to medium acidity, highly resistant to *Colletotrichum fragariae.*

Specifically, Table 1 below shows a comparison between the instant variety 'YUKAGUYA' and the comparative variety 'TOCHIOTOME' (PVP granted in Japan, No. 5248).

TABLE 1

Comparison between 'YUKAGUYA' and 'TOCHIOTOME'

| No. | Characteristics | Reference variety 'TOCHIOTOME' States | Present variety 'YUKAGUYA' States |
|---|---|---|---|
| 9 | Leaf: size | medium (135.5 $cm^2$) | large (157.8 $cm^2$) |
| 19 | Petiole: length | short (10.4 cm) | long (20.5 cm) |
| 35 | Fruit: size | medium to large (15.5 g) | large to very large (20.3 g) |
| 45 | Fruit: position of achenes | deep below surface | level with surface |

Table 2 below shows a comparison between the instant variety 'YUKAGUYA' and the comparative variety 'KOIMINORI' (PVP granted in Japan, No. 28183).

TABLE 2

Comparison between 'YUKAGUYA' and 'KOIMINORI'

| No. | Characteristics | Reference variety 'KOIMINORI' States | Present variety 'YUKAGUYA' States |
|---|---|---|---|
| 53 | Fruit: color of flesh | white (RHS NN155D) | vivid reddish orange (RHS 33B) |
| 57 | Time of beginning of fruit ripening | medium (December 19) | early (November 29) |

Further, Table 3 below shows a comparison between the instant variety 'YUKAGUYA' and its female parent '12164-02':

TABLE 3

Comparison between 'YUKAGUYA' and '12164-02'

| No. | Characteristics | Female parent variety '12164-02' States | Present variety 'YUKAGUYA' States |
|---|---|---|---|
| 19 | Petiole: length | short (13.9 cm) | long (23.1 cm) |
| 22 | Inflorescence: number of flowers | medium (7.5/plant) | many (14.0/plant) |
| 52 | Fruit: firmness | medium (1.7N/3 mmφ) | very firm (2.4N/3 mmφ) |
| 60 | Fruit: acidity | high (0.66%) | low (0.34%) |

Further, Table 4 below shows a comparison between the instant variety 'YUKAGUYA' and its male parent 'KUMAMOTO VS03':

TABLE 4

Comparison between 'YUKAGUYA' and 'KUMAMOTO VS03'

| No. | Characteristics | Male parent variety 'KUMAMOTO VS03' States | Present variety 'YUKAGUYA' States |
|---|---|---|---|
| 2 | Plant: density of foliage | dense | medium |
| 17 | Terminal leaflet: size | large | medium |
| 24 | Stipule: anthocyanin coloration | weak to medium | medium to strong |
| 34 | Fruit: size | medium to large | large to very large |
| 44 | Fruit: width of band without achenes | narrow | absent or very narrow |
| 52 | Fruit: adherence of calyx | medium | medium |
| 60 | Fruit: soluble solids content | medium to high | high to very high |

BRIEF DESCRIPTION OF THE DRAWINGS

In the accompanying drawings, which are as nearly true as is reasonable possible to make in a color illustration of this type.

Figure 1:
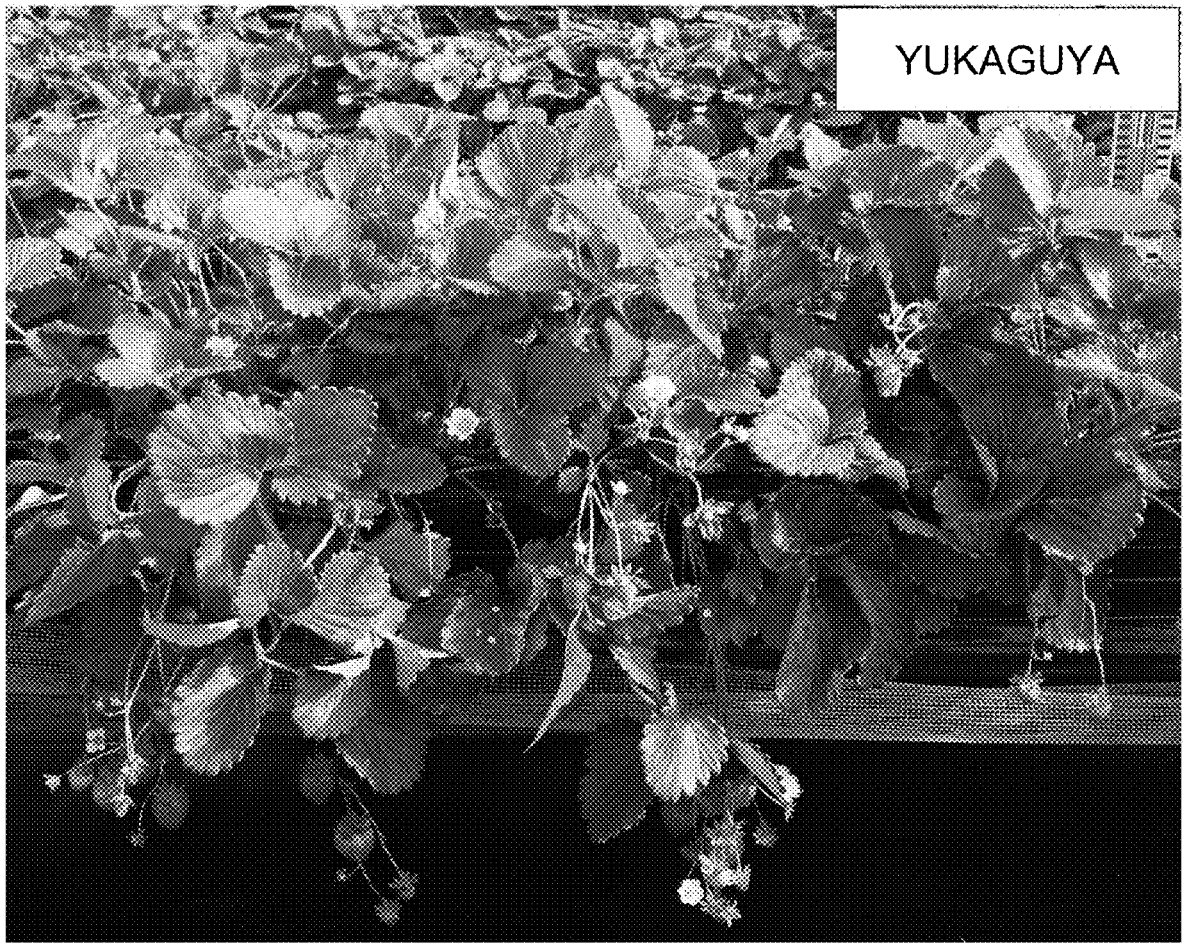
FIG. 1 is a color photograph showing a general view of an illustrative Strawberry plant of the variety named 'YUKAGUYA' bearing fruits; the age of the plant was 101 days after transplanting seedlings into the greenhouse.
Figure 2:
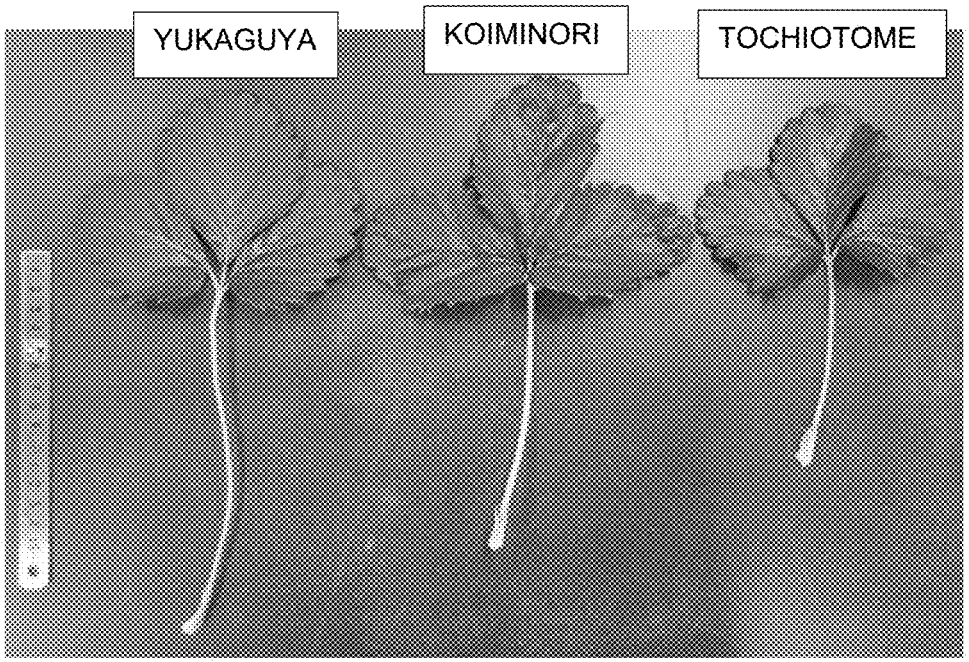
FIG. 2 is a color photograph showing leaves of 'YUKAGUYA', 'KOIMINORI' and 'TOCHIOTOME'.
Figure 3:
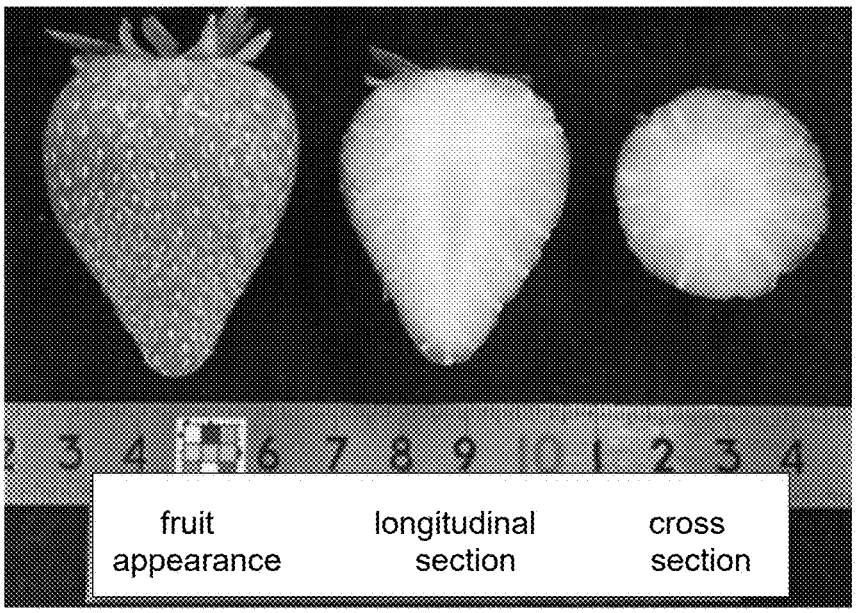
FIG. 3 is a color photograph showing fruits of 'YUKAGUYA' (left: fruit appearance, middle: longitudinal section, right: cross section).
Figure 4:
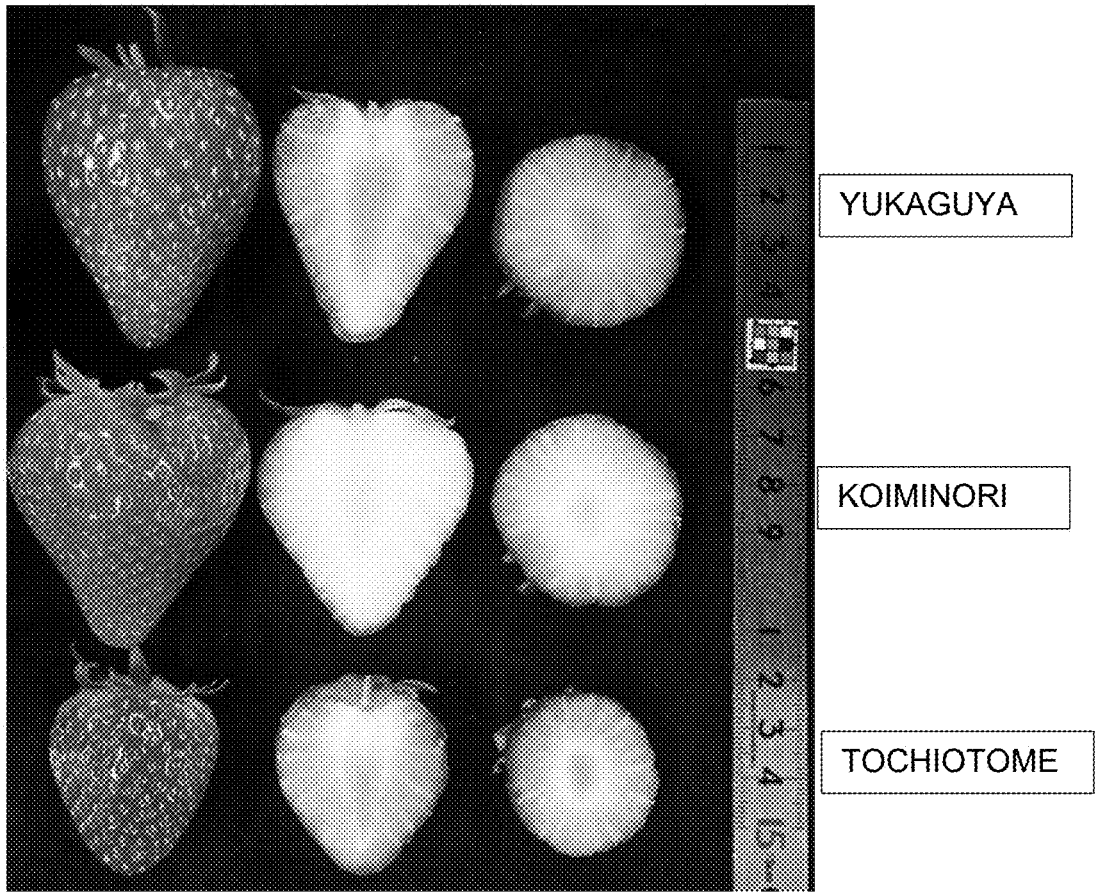
FIG. 4 is a color photograph showing fruits of 'YUKAGUYA', 'KOIMINORI' and 'TOCHIOTOME' (left: fruit appearance, middle: longitudinal section, right: cross section).

Due to chemical and/or digital development, processing and printing, the plants or portions of plants depicted in the photographs may or may not be precisely accurate, when compared to the actual botanical specimens.

DETAILED DESCRIPTION OF THE INVENTION

Table 3 below shows the botanical description of the 'YUKAGUYA' plants evaluated from 2022 to 2024 (including the comparison with the reference plant 'TOCHIOTOME' and 'KOIMINORI'). The values provided are averages. The location of the plants evaluated was Kurume-city, Fukuoka, Japan.

The 'YUKAGUYA' plants shown on the photographs were grown at Kuruma-city, Fukuoka, Japan. The plants were grown at elevated bed in green house. The age of the plants were 101-124 days after transplanting seedlings into the greenhouse. The plants were photographed on Jan. 4, 2024, the leaves were photographed on Apr. 18, 2024, and the fruits were photographed on Apr. 9, 2024.

Colors are given according to The R.H.S. (Royal Horticultural Society) Colour Chart, Sixth edition, 2019 reprint.

BOTANICAL DESCRIPTION

TABLE 5

Botanical description of 'YUKAGUYA'

| No. | Characteristics | Descriptions | Values |
|---|---|---|---|
| 1. | Plant: growth habit | upright | |
| 2. | Plant: density of foliage | medium | |
| 3. | Plant: vigor | medium to strong | |
| 4. | Plant: number of axillary buds | medium | 2.9 |
| 5. | Plant: position of inflorescence in relation to foliage | same level | |
| 6. | Plant: number of stolons | medium | 12.0 |
| 7. | Stolon: anthocyanin coloration | weak | |
| 8. | Stolon: density of pubescence | medium | |
| 9. | Flowering runners | absent | |
| 10. | Leaf: size | large | 157.8 $cm^2$ |
| 11. | Leaf: length | | 20.3 cm |
| 12. | Leaf: width | | 8.2 cm |
| 13. | Leaf: color of upper side | moderate green | RHS 135B |
| 14. | Leaf: blistering | absent or weak | |
| 15. | Leaf: glossiness | medium | |
| 16. | Leaf: variegation | absent | |
| 17. | Terminal leaflet: size | medium | 77.7 $cm^2$ |
| 18. | Terminal leaflet: length in relation to width | moderately longer | 1.26 |
| 19. | Terminal leaflet: shape of base | acute | |
| 20. | Terminal leaflet: margin | serrate to crenate | |
| 21. | Terminal leaflet: shape in cross section | concave | |
| 22. | Petiole: length | long | 20.5 cm |

TABLE 5-continued

Botanical description of 'YUKAGUYA'

| No. | Characteristics | Descriptions | Values |
|---|---|---|---|
| 23. | Petiole: attitude of hairs | horizontal | |
| 24. | Stipule: anthocyanin coloration | medium to strong | |
| 25. | Inflorescence: number of flowers | medium to many | 13.6 |
| 26. | Peduncle: length | long | 16.8 cm |
| 27. | Pedicel: attitude of hairs | slightly outwards | |
| 28. | Flower: diameter | medium to large | 2.9 cm |
| 29. | Flower: arrangement of petals | overlapping | |
| 30. | Flower: size of calyx in relation to corolla | same size | |
| 31. | Flower: stamen | present | |
| 32. | Petal: length in relation to width | equal | 1.05 |
| 33. | Petal: color of upper side | white | RHS NN155C |
| 34. | Fruit: size | large to very large | 23.2 g |
| 35. | Fruit: length | | 4.0 cm |
| 36. | Fruit: width | | 3.3 cm |
| 37. | Fruit: length in relation to width | moderately longer | 1.30 |
| 38. | Fruit: shape | conical | |
| 39. | Fruit: difference in shape of terminal and other fruits | slight to moderate | |
| 40. | Fruit: color | vivid reddish orange | RHS 40B |
| 41. | Fruit: evenness of color | even or very slightly | |
| 42. | Fruit: glossiness | strong | |
| 43. | Fruit: evenness of surface | even or very slightly | |
| 44. | Fruit: width of band without achenes | absent or very narrow | |
| 45. | Fruit: neck | absent | |
| 46. | Fruit: position of achenes | level with surface | |
| 47. | Fruit: density of achenes | medium | |
| 48. | Fruit: anthocyanin coloration of achenes | weak | |
| 49. | Fruit: position of calyx attachment | level with fruit | |

TABLE 5-continued

Botanical description of 'YUKAGUYA'

| No. | Characteristics | Descriptions | Values |
|---|---|---|---|
| 50. | Fruit: attitude of sepals | outwards | |
| 51. | Fruit: diameter of calyx in relation to diameter of fruit | same size | |
| 52. | Fruit: adherence of calyx | medium | |
| 53. | Fruit: firmness | firm to very firm | 2.7 n/3 mm |
| 54. | Fruit: color of flesh (excluding core) | vivid reddish orange | RHS 33B |
| 55. | Fruit: color of core | vivid reddish orange | RHS 33B |
| 56. | Fruit: cavity | absent or small | |
| 57. | Time of beginning of flowering | early | October 31 |
| 58. | Time of beginning of fruit ripening | early | November 29 |
| 59. | Type of bearing | not remontant | |
| 60. | Fruit: soluble solids content | high to very high | 10.6 Brix |
| 61. | Fruit: acidity | low to medium | 0.55% |
| 62. | Dormant period | short | |
| 63. | Resistance to *Colletotrichum fructicola* (Nara-gc-d) or *Colletotrichum* sp. GC-7 | highly resistant | |
| 64. | Resistance to *Fusarium oxysporum* f. sp. *fragariae* | moderately resistant | |

Other features of the plant are as follows:

Growing tests were conducted in a plant factory with artificial light, comparing this variety with existing varieties. The new variety was found to be suitable for cultivation in a plant factory, as it had a higher sugar content in its fruit than other existing varieties, had excellent yields, and had a low incidence of deformed fruit.

We claim:

1. A new and distinct variety of *Fragaria* L. plant named 'YUKAGUYA', substantially as described and illustrated herein.

* * * * *